(12) United States Patent
Ryan et al.

(10) Patent No.: US 8,795,319 B2
(45) Date of Patent: Aug. 5, 2014

(54) EMBOLIZATION COIL

(75) Inventors: Chelsey Elizabeth Ryan, Bloomington, IN (US); Arman Valaie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 183 days.

(21) Appl. No.: 13/038,968

(22) Filed: Mar. 2, 2011

(65) Prior Publication Data

US 2012/0226304 A1    Sep. 6, 2012

(51) Int. Cl.
*A61M 29/00* (2006.01)

(52) U.S. Cl.
USPC ........................................... 606/200

(58) Field of Classification Search
CPC ..................... A61B 17/12009; A61B 17/1214; A61B 17/1215; A61B 17/12145; A61B 17/12181; A61B 17/1219
USPC ............................ 606/191, 200; 128/831, 843
See application file for complete search history.

(56) References Cited

U.S. PATENT DOCUMENTS

| 5,417,708 | A | | 5/1995 | Hall et al. |
|---|---|---|---|---|
| 5,725,534 | A | | 3/1998 | Rasmussen |
| 5,782,860 | A | | 7/1998 | Epstein et al. |
| 5,797,953 | A | | 8/1998 | Tekulve |
| 6,024,765 | A | * | 2/2000 | Wallace et al. ............... 606/191 |
| 6,117,157 | A | | 9/2000 | Tekulve |
| 6,261,679 | B1 | * | 7/2001 | Chen et al. ............... 428/317.9 |
| 6,296,604 | B1 | | 10/2001 | Garibaldi et al. |
| 6,358,228 | B1 | | 3/2002 | Tubman et al. |
| 6,551,340 | B1 | | 4/2003 | Kónya et al. |
| 6,585,756 | B1 | | 7/2003 | Strecker |
| 6,602,261 | B2 | * | 8/2003 | Greene et al. ............... 606/108 |
| 6,939,337 | B2 | | 9/2005 | Parker et al. |
| 7,520,894 | B2 | | 4/2009 | Pavcnik et al. |
| 7,597,710 | B2 | | 10/2009 | Obermiller |

(Continued)

FOREIGN PATENT DOCUMENTS

| CN | 101066219 A | 11/2007 |
|---|---|---|
| JP | 02/031762 | 2/1990 |

(Continued)

OTHER PUBLICATIONS

"Sugi", Kettenbach GmbH & Co. KG, 2008-2010, 6 pages.

(Continued)

*Primary Examiner* — Darwin Erezo
*Assistant Examiner* — Martin T Ton
(74) *Attorney, Agent, or Firm* — Brinks Gilson & Lione

(57) ABSTRACT

An occluding device for occlusion of fluid flow through a body cavity is disclosed. The device comprises an embolization coil formed from at least one wire strand and having an initial tension. The embolization coil is defined by a primary coil formed into a secondary coil. The primary coil has a primary shape defined by a linear longitudinally extending coil having a plurality of helical turns and is helically wound into the secondary coil, wherein the secondary coil has a series of axially spaced apart loops. The axially spaced apart loops are larger than the helical turns of the primary coil. The embolization coil is movable between an expanded state for occlusion of a body cavity and a collapsed state for delivery or retrieval. An absorbent material, including at least one of cotton and regenerated cellulose, is attached to the embolization coil and extends therefrom. A kit is also included.

15 Claims, 6 Drawing Sheets

(56) References Cited

U.S. PATENT DOCUMENTS

| | | |
|---|---|---|
| 2002/0032408 A1 | 3/2002 | Parker et al. |
| 2003/0216772 A1 | 11/2003 | Konya et al. |
| 2004/0138695 A1 | 7/2004 | Li et al. |
| 2004/0210301 A1 | 10/2004 | Obermiller |
| 2005/0004598 A1* | 1/2005 | White et al. .................. 606/200 |
| 2005/0143807 A1 | 6/2005 | Pavcnik et al. |
| 2006/0142846 A1 | 6/2006 | Pavcnik et al. |
| 2006/0206139 A1 | 9/2006 | Tekulve |
| 2006/0259130 A1 | 11/2006 | Tabata et al. |
| 2007/0082021 A1 | 4/2007 | Bates |
| 2007/0083257 A1 | 4/2007 | Pal et al. |
| 2007/0225738 A1 | 9/2007 | Pal |
| 2007/0233175 A1 | 10/2007 | Zaver et al. |
| 2008/0188892 A1 | 8/2008 | Bates et al. |
| 2008/0200944 A1 | 8/2008 | Hardert |
| 2009/0029261 A1 | 1/2009 | Thomas-Alyea et al. |
| 2009/0048662 A1 | 2/2009 | Pavcnik et al. |
| 2009/0054905 A1 | 2/2009 | Levy |
| 2009/0062838 A1 | 3/2009 | Brumleve et al. |
| 2009/0062844 A1 | 3/2009 | Tekulve et al. |
| 2009/0062845 A1 | 3/2009 | Tekulve |
| 2009/0204145 A1 | 8/2009 | Matthews |
| 2009/0216263 A1 | 8/2009 | Tekulve |
| 2009/0270908 A1 | 10/2009 | Tekulve et al. |
| 2009/0270978 A1 | 10/2009 | Virkler et al. |
| 2010/0004672 A1 | 1/2010 | Shirley et al. |
| 2010/0010533 A1 | 1/2010 | Burke et al. |
| 2010/0030246 A1 | 2/2010 | Pavcnik et al. |
| 2010/0030259 A1 | 2/2010 | Pavcnik et al. |
| 2010/0152650 A1 | 6/2010 | Schrodt |
| 2010/0204683 A1 | 8/2010 | Bodor et al. |
| 2010/0312272 A1 | 12/2010 | Pavcnik et al. |
| 2010/0312321 A1 | 12/2010 | Kiyosue et al. |

FOREIGN PATENT DOCUMENTS

| | | |
|---|---|---|
| JP | 10-127754 | 5/1998 |
| WO | WO 95/25480 | 9/1995 |
| WO | WO 03/037423 A1 | 5/2003 |
| WO | WO 2006/042114 | 4/2006 |
| WO | WO 2008/106171 | 9/2008 |
| WO | WO 2010/096717 A1 | 8/2010 |
| WO | WO 2010/101031 A1 | 10/2010 |

OTHER PUBLICATIONS

"Embolization Coils", Cook Medical, 2008, 16 pages.
U.S. Appl. No. 11/664,903, filed May 7, 2009, Hunt.

* cited by examiner

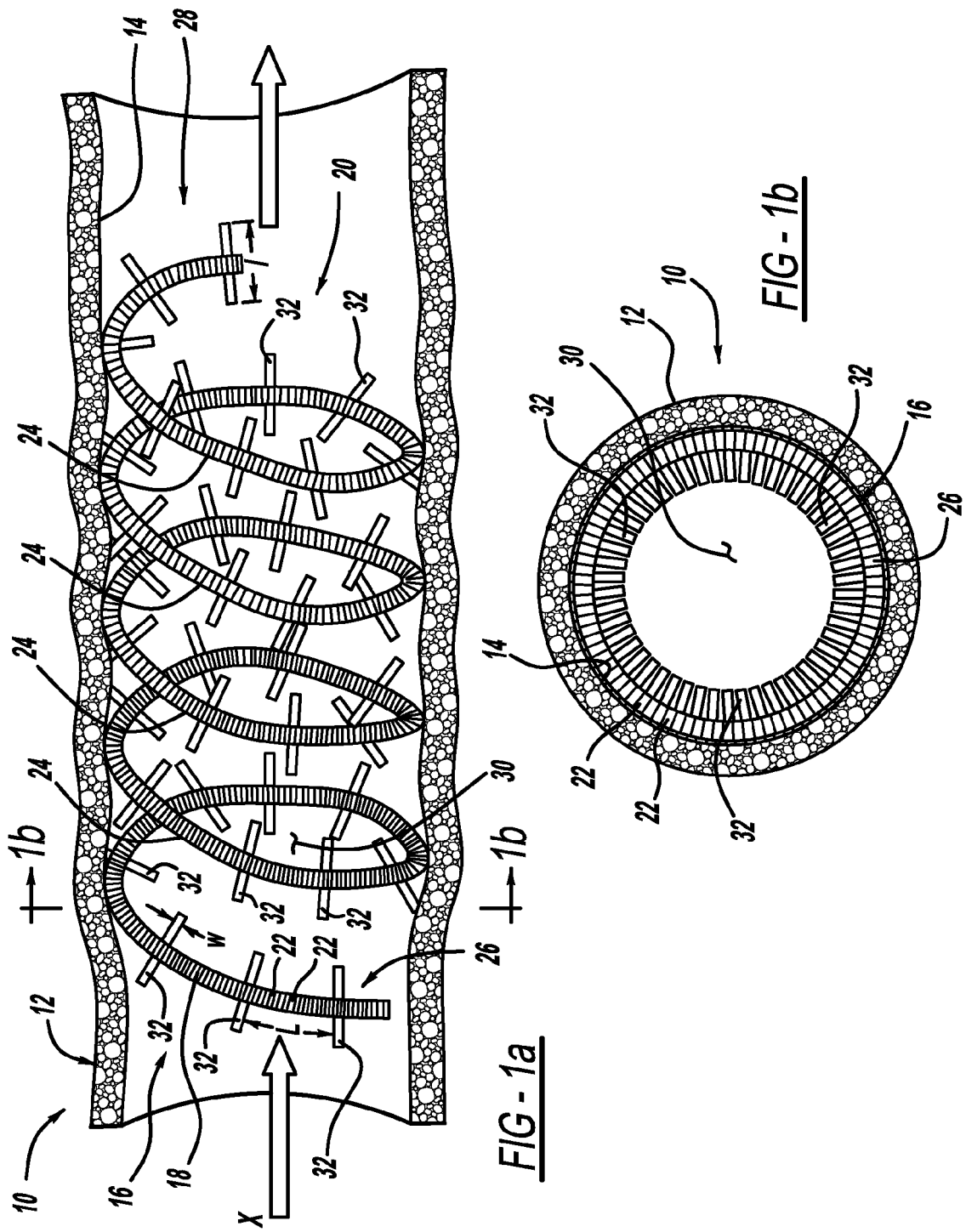

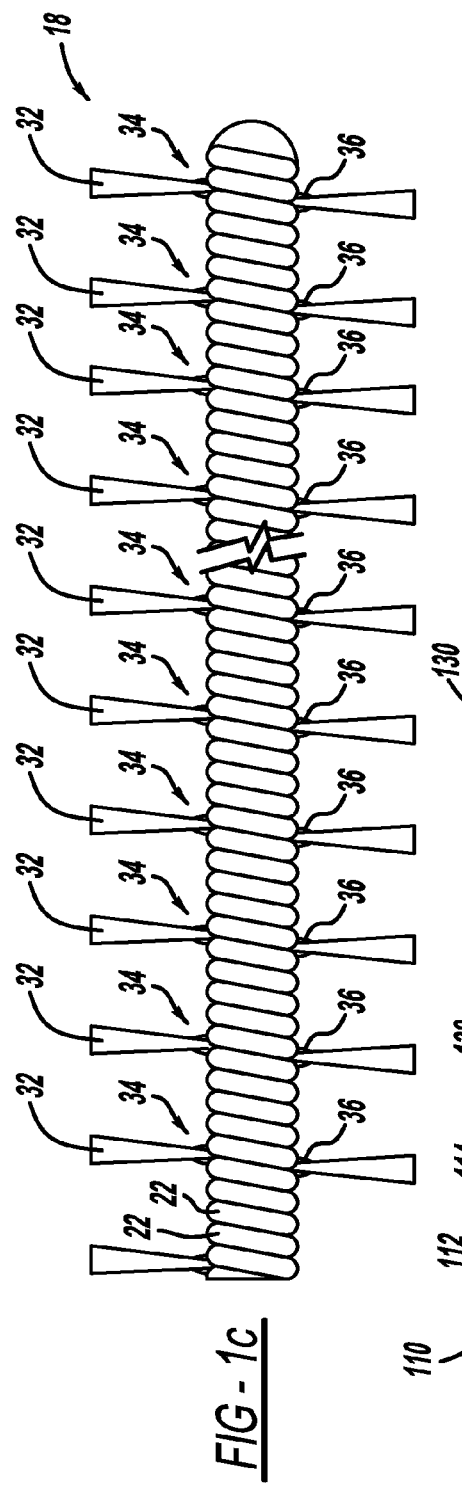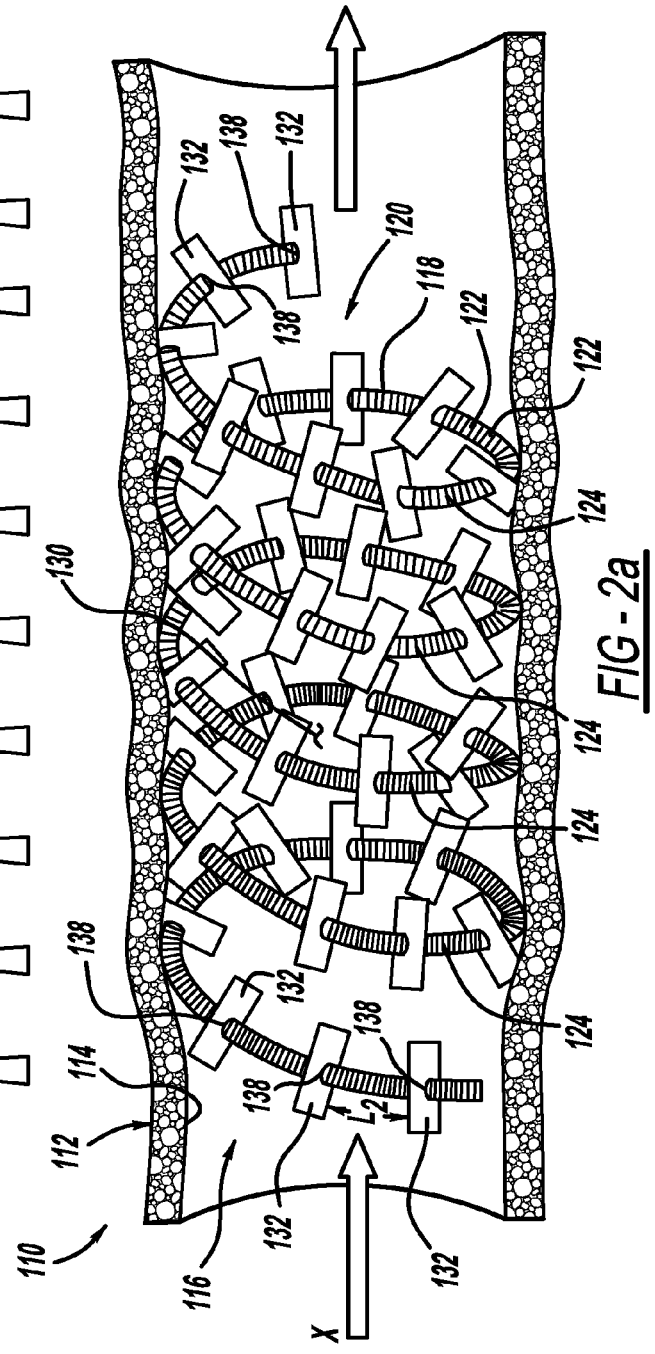

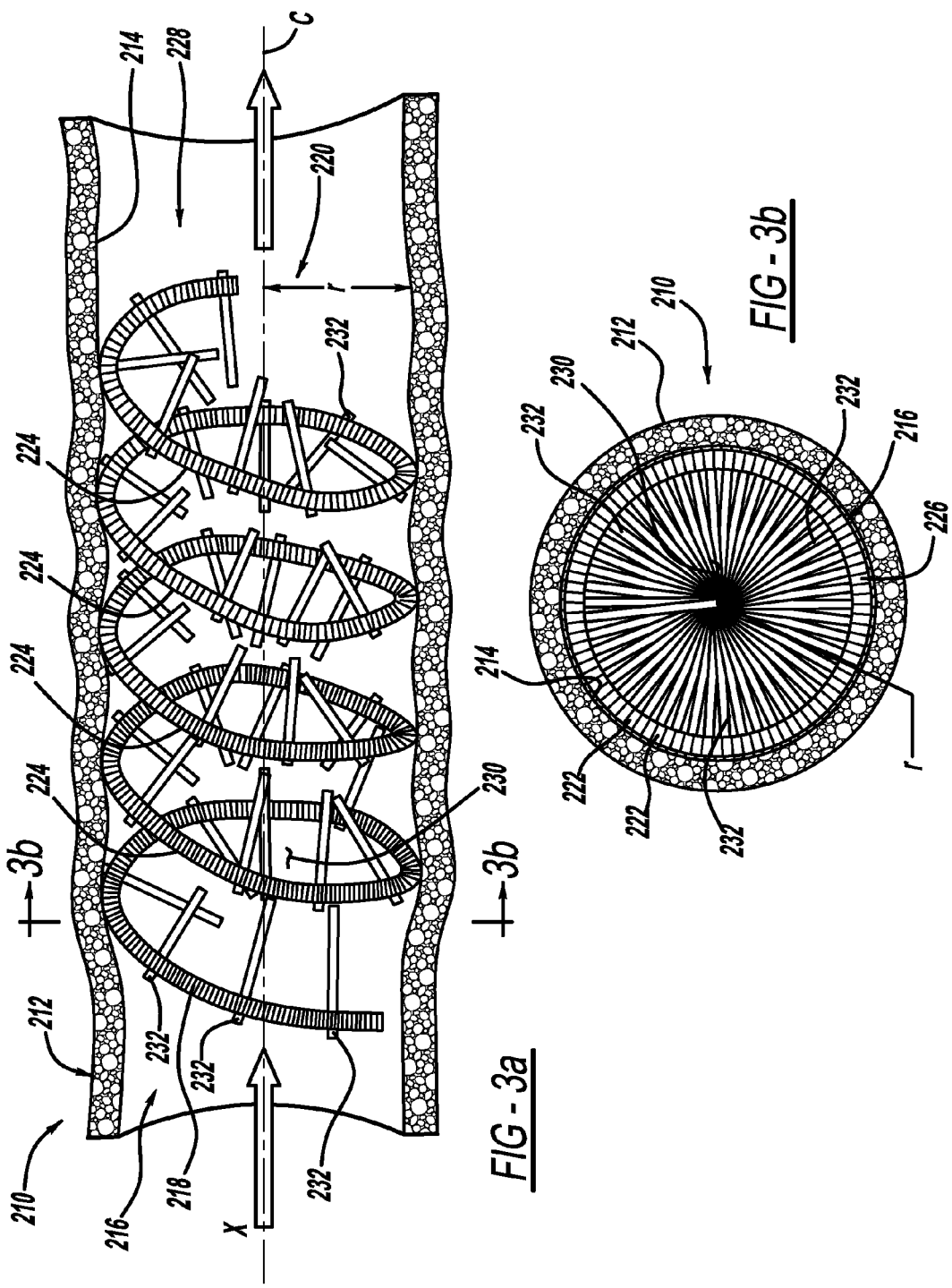

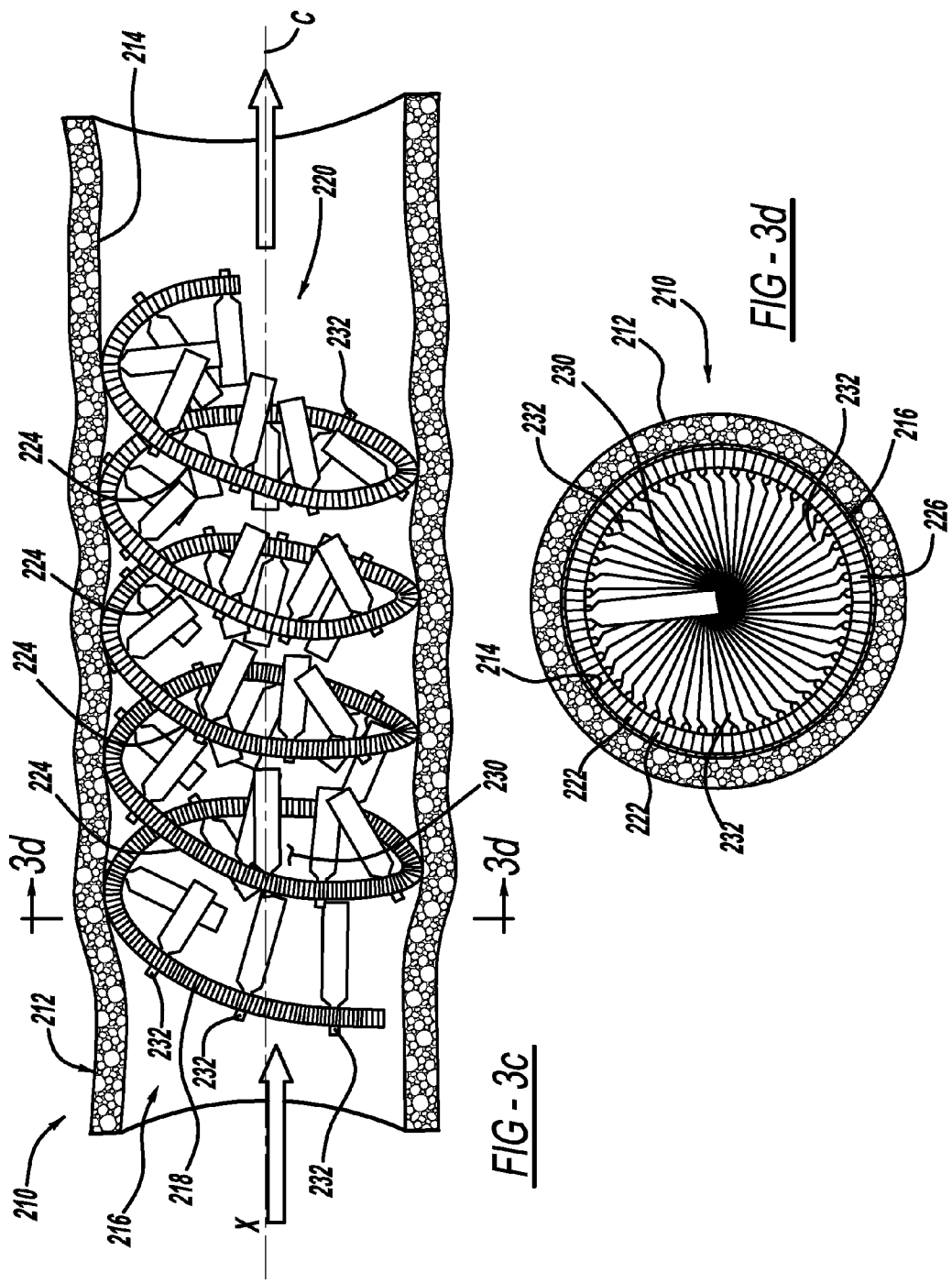

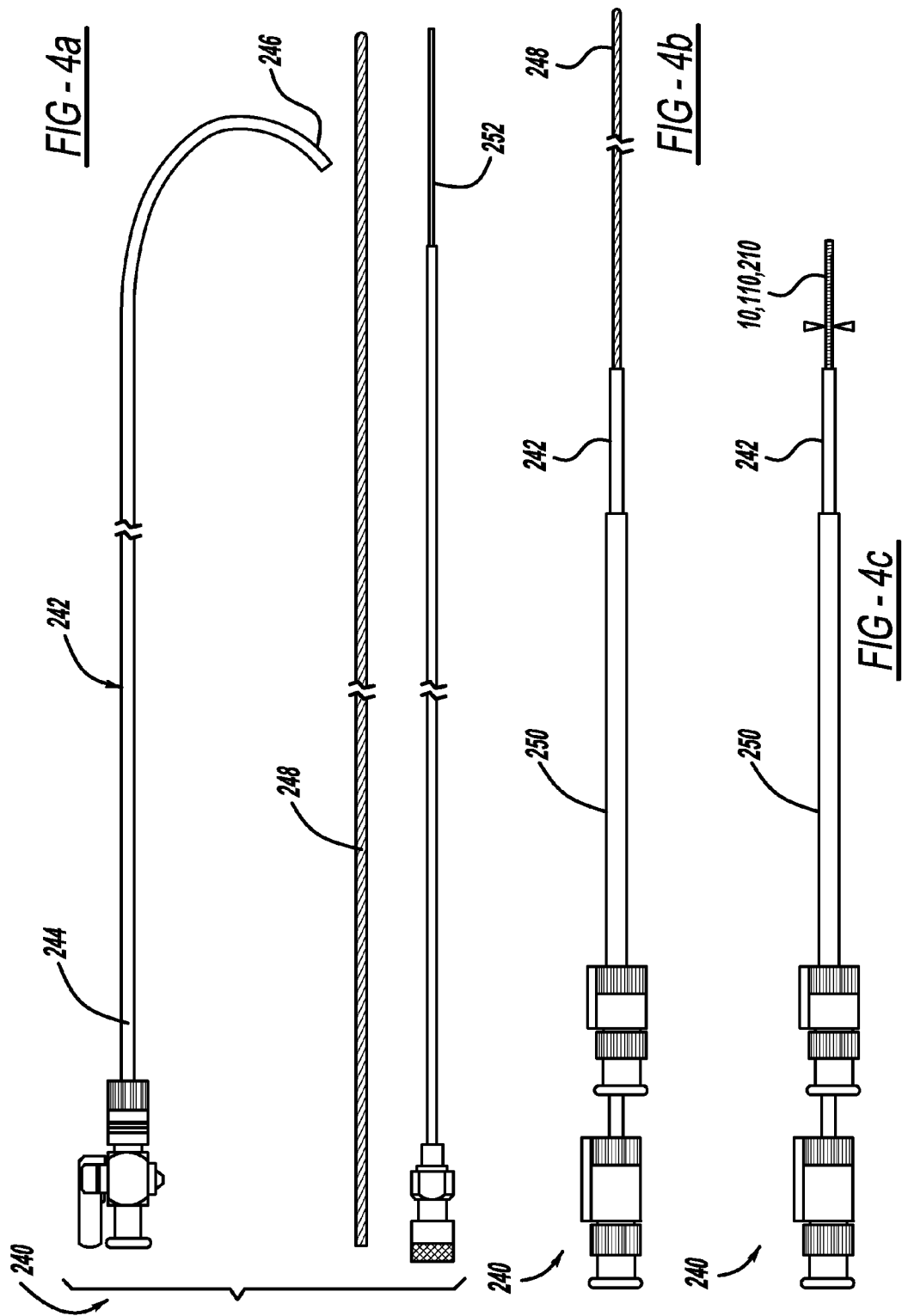

EMBOLIZATION COIL

BACKGROUND OF THE INVENTION

The present invention relates to medical devices. More particularly, the invention relates to occluding devices that include a coil and occluding material.

Pushable fibered coils have been used as a primary occluding device for treatment of various arteriovenous malformations (AVM) and varicoceles, as well as for many other arteriovenous abnormalities in the body. Occluding devices are also used to repair abnormal shunts between arteries and veins, prevent or reduce blood flow to tumors, stop hemorrhaging as a result of trauma, and stabilize aneurysms to prevent rupture. Pushable fibered coils may be configured in a variety of sizes with varying diameters and may be made of several different materials including stainless steel and platinum. Occlusion devices may vary for differing purposes, e.g., to hold the device in place within a cavity or vessel and to pack the device within the vessel for enhanced occlusion.

Although current pushable fibered coils are adequate, such coils may be improved for more effective occlusion of fluid flow through a lumen of a body vessel. Many medical procedures for occluding blood flow through an artery or vein require a number of coils having a relatively large cross-sectional profile. Moreover, one coil or two may not be sufficient to effectively occlude blood flow through a lumen of an artery or vein. In many current procedures, many coils may deployed serially within a body vessel, and/or the coils may be packed within each other to produce effective cross sectional occlusion of fluid flow through a body vessel. In some instances, these procedures may involve an undesirable amount of additional time and costs.

BRIEF SUMMARY OF THE INVENTION

The present invention generally provides an occluding device that provides an enhanced occluding ability by providing a structure bearing absorbent material that can absorb liquid in a weight and/or volume much greater than the weight and/or volume of the occluding material.

In one embodiment, the present invention provides an occluding device for occlusion of a body cavity or vessel. The device comprises an embolization coil formed from at least one wire strand. The embolization coil has a proximal portion and a distal portion extending longitudinally from the proximal portion and an initial tension along the distal and proximal portions. The embolization coil is defined by a primary coil formed into a secondary coil. The primary coil has a primary shape defined by a linear longitudinally extending coil having multiple helical turns. The primary coil is helically wound into the secondary coil. The secondary coil has a series of axially spaced apart loops, which are helical turns, that are larger than the helical turns of the primary coil. The embolization coil is movable between an expanded state for occlusion of a body cavity and a collapsed state for delivery or retrieval. The occluding device further includes absorbent material attached to the embolization coil, and the absorbent material extends from the embolization coil. The absorbent material includes cotton, regenerated cellulose, or both, for occlusion of the body cavity.

In another embodiment, an occluding device for occlusion of a body cavity is provided that includes an embolization coil and strips of absorbent material. The embolization coil has a proximal portion and a distal portion extending longitudinally from the proximal portion and an initial tension along the distal and proximal portions. The embolization coil is defined by a primary coil formed into a secondary coil. The primary coil has a primary shape defined by a linear longitudinally extending coil and is helically wound into the secondary coil. The secondary coil has a secondary shape defined by a spiral shaped coil having a series of axially spaced loops. The embolization coil is movable between an expanded state for occlusion of a body cavity and a collapsed state for delivery or retrieval. Several strips of absorbent material are attached to the embolization coil, and the strips extend from the embolization coil. Each strip has a pair of flat opposed sides. The strips are spaced apart longitudinally along the embolization coil for occlusion of the body cavity.

In yet another form, the present invention provides an occluding device for occlusion of a body cavity that includes a coil and strips. The coil has a proximal portion and a distal portion extending longitudinally from the proximal portion. The coil is movable between an expanded state for occlusion of a body cavity and a collapsed state for delivery or retrieval. Multiple strips of expandable material are attached to the coil and extend therefrom. The strips of expandable material are spaced apart longitudinally along the coil for occlusion of the body cavity. Each strip of expandable material includes regenerated cellulose and cotton.

In still another embodiment, the present invention provides an occluding device for occlusion of a body cavity including a coil and a plurality of sheets of expandable material. The coil has a proximal portion and a distal portion extending longitudinally from the proximal portion, and the coil is movable between an expanded state for occlusion of a body cavity and a collapsed state for delivery or retrieval. The coil defines an inner lumen in the expanded state. The sheets of expandable material are attached to the coil and extend into the inner lumen. Each sheet has a pair of flat opposed sides. The sheets of expandable material are configured to absorb bodily fluid and expand from an original size to an expanded size. When in the expanded size, the sheets form a barrier across the inner lumen for occlusion of the body cavity.

In still another embodiment, the present invention provides an embolization kit for occluding fluid flow through a body vessel. The kit includes a guide catheter, an inner catheter, and an occluding device. The inner catheter has proximal and distal ends and is configured to be passed through the guide catheter to position the inner catheter in the body vessel. The inner catheter has a hub adjacent the proximal end. The occluding device is disposed coaxially within the inner catheter. The occluding device includes a coil having a proximal portion and a distal portion extending longitudinally from the proximal portion and an initial tension along the distal and proximal portions. The coil is movable between an expanded state for occlusion of a body cavity and a collapsed state for delivery or retrieval. Multiple strips of expandable material are attached to the coil and extend therefrom. The strips of expandable material are spaced apart longitudinally along the coil for occlusion of the body cavity. Each strip of expandable material includes regenerated cellulose and cotton.

Further objects, features, and advantages of the present invention will become apparent from consideration of the following description and the appended claims when taken in connection with the accompanying drawings. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

FIG. 1a is an environmental side view of an occluding device deployed in a body vessel in accordance with one embodiment of the present invention;

FIG. 1b is a cross-sectional view of the occluding device of FIG. 1a, taken along line 1b-1b in FIG. 1a;

FIG. 1c is a side view of a primary coil of the occluding device of FIGS. 1a-1b in accordance with one embodiment of the present invention;

FIG. 2a is an environmental side view of an occluding device deployed in a body vessel in accordance with another embodiment of the present invention;

FIG. 3a is an environmental side view of an occluding device deployed in a body vessel in accordance with another embodiment of the present invention;

FIG. 3b is a cross-sectional view of the occluding device of FIG. 3a, taken along line 3b-3b in FIG. 3a;

FIG. 3c is an environmental side view of the occluding device of FIGS. 3a-3b having absorbent material that has expanded within the body vessel, in accordance with the principles of the present invention;

FIG. 3d is a cross-sectional view of the occluding device of FIG. 3c, taken along line 3d-3d in FIG. 3c;

FIG. 4a is an exploded view of an embolization kit for an occluding device in accordance with one embodiment of the present invention;

FIG. 4b is a side view of the embolization kit of FIG. 4a; and

FIG. 4c is a side view of the embolization kit of FIGS. 4a-4b, including showing the occluding device in a partially deployed position.

DETAILED DESCRIPTION OF THE INVENTION

Figure 2B:
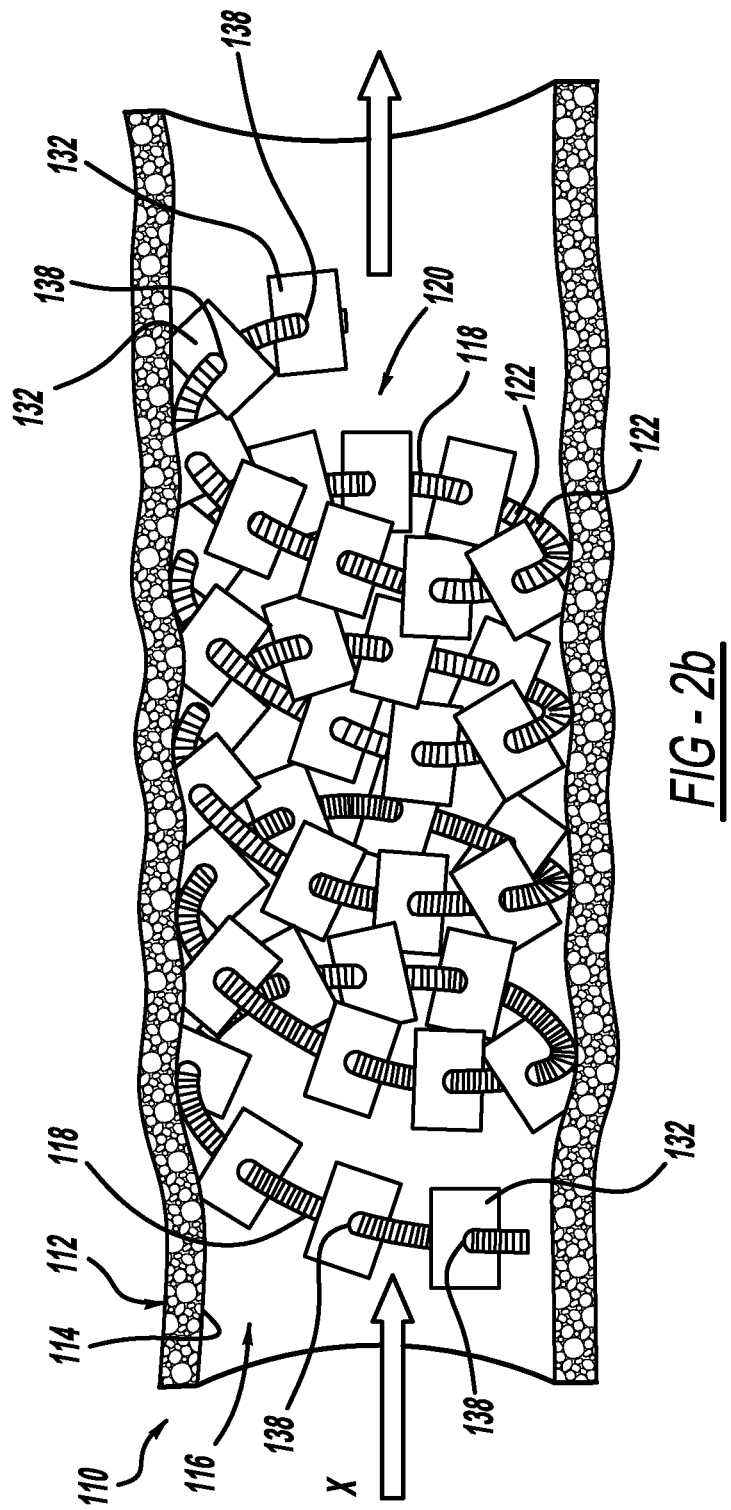
FIG. 2b is an environmental side view of the occluding device of FIG. 2a having absorbent material that has expanded within the body vessel, in accordance with the principles of the present invention.

The following description is merely exemplary in nature and is not intended to limit the present disclosure, application, or uses.

The present invention generally provides an occluding device having enhanced occluding features, including expandable, absorbable material that can hold many times the weight of the material in bodily fluids. The absorbable material grows in size and volume as absorbs bodily fluids. The device comprises a coil and is used for transcatheter embolization.

The occluding device may be used to occlude fluid flow through a body vessel or body cavity due to a blood vessel malformation occurring in the brain, like aneurysms, or another part of the body. The occluding device also may be used for treatment of renal arteriovenous malfunction (AVM), pulmonary AVM, vascular tumors, low-flow fistulas, trauma related hemorrhages, and visceral vasculature defects including varicoceles, and aneurysms. For example, treatment of visceral vasculature defects may include but are not limited to embolotherapy on gastroduodenal hemorrhages, hepatic aneurysms, celiac aneurysms, internal iliac aneurysms, and internal spermatic varicoceles.

Referring now to FIGS. 1a-1b, an occluding device 10 is illustrated in a deployed state for occlusion of fluid flow through a lumen of a body vessel 12 in accordance with one embodiment of the present invention. As shown in FIGS. 1a-1b, the occluding device 10 is positioned to engage an inner wall 14 of the body vessel 12 and comprises an embolization coil 16 formed from at least one wire strand. The embolization coil 16 is movable between an expanded state for occlusion of a body cavity, as shown in FIGS. 1a-1b, and a collapsed state for delivery or retrieval of the occluding device 10 (see FIG. 4c).

The embolization coil 16 includes a primary coil 18 wound into a secondary coil 20. The primary coil 18 has a primary shape defined by a linear longitudinally extending coil having a plurality of helical turns 22. The helical turns 22 are a series of tightly wound helical turns 22, wherein each helical 22 turn touches the helical turn 22 next to it. Thus, the helical turns 22 are tightly spaced, in this embodiment.

The primary coil 18 is formed into a helical shape to form the secondary coil 20, wherein the loops 24 of the secondary coil 20 do not contact each other in the expanded state of the occluding device 10. Thus, the secondary coil 20 has a series of axially spaced apart loops 24, wherein the axially spaced apart loops 24 are larger than the helical turns 22 of the primary coil 18. The loops 24 may be spaced apart by a predetermined distance, for example, by about four to five millimeters curl space, in some embodiments, wherein the curl space is defined as the distance between two loops 24. It should be understood, however, that the loops 24 of the secondary coil 20 could contact each other in the expanded state, without falling beyond the spirit and scope of the present invention. Likewise, the helical turns 22 of the primary coil 18 need not contact each other in all embodiments of the present invention.

The embolization coil 18 has a proximal portion 26 and a distal portion 28 integrally extending longitudinally from the proximal portion 26. The embolization coil 16 has an initial tension along the distal and proximal portions 26, 28. The initial tension of the primary coil 18 provides ability for the occluding device 10 to fold and unfold between the collapsed state and the expanded state. The series of loops 24 of the secondary coil 20 define a cross-sectional lumen 30 through the embolization coil 16 (see FIG. 1b). In this embodiment, the lumen 30 has a generally circular cross-sectional shape.

The embolization coil 16 may be made from any suitable material, such as a metal or alloy, and preferably it is made from platinum or stainless steel. The embolization coil 16 may have an initial tension between about 5 to 60 grams of weight, and preferably between about 10 to 30 grams of weight. Initial tension may be defined to be the amount of force required to cause a four centimeter length of coil to begin to collapse. The initial tension may also be defined by the amount of force required to cause a coil to begin elongating at a ratio of between about 1.25 to 15 grams per centimeter. Without limiting the invention, it is believed that the initial tension of the coil provides the occluding device 10 the capability of being folded across the diameter of a lumen of a body vessel 12 after deployment from a catheter, which may be desirable in some embodiments.

The embolization coil 16 may be made by any apparatus known in the art. For example, the embolization coil 16 may be made by a coil winding machine such as a roller deflecting apparatus, a mandrel apparatus, or any other suitable means. The coil 16 could have a length of between about 3 to 20 centimeters, but the coil 16 need not be limited to this range. As shown in FIG. 1a, the secondary coil 20 may have an outer diameter ranging between about 3 and 15 millimeters. The primary coil 18 may have a diameter of between about 0.010 and 0.35 inch. The catheter diameter through which the occluding device 10 may be advanced may range between about 0.014 and 0.027 inch, by way of example.

In accordance with various embodiments, the distal portion 28 of the occluding device 10 may have a less, the same, or a greater outside diameter than the proximal portion 26. The proximal portion 26 may have a variable outside diameter along the length of the secondary coil 16, creating the series of loops 24 with variable diameter. In other words, the series of loops 24 need not all have the same outside diameter, although in the embodiment of FIGS. 1a-1b, they do have substantially the same outside diameter. In some embodiments, the loops 24 at the proximal end 26 could have a diameter that touches the vessel wall 14 at a largest diameter of the occluding device 10, and each loop 24 along the device 10 in the X direction could be smaller than the loop 24 before it, and the last loop 24 at the distal portion 28 could be small, for example, half the size of the first loop 24 on the proximal portion 26, and located near the center of the lumen 30. In this way, the lumen 30 would be substantially blocked by loops 24.

The occluding device 10 includes absorbent, expandable material, such as a sponge material, attached to the embolization coil 16. In this embodiment, the absorbent material is in the form of a plurality of strips 32 of absorbent material attached to the embolization coil 16 and extending therefrom. With reference to the figures, only some of the strips 32 are labeled, to avoid cluttering the figures with a large duplication of reference numbers. It should be understood, however, that the absorbent material could take on any other suitable form, without falling beyond the spirit and scope of the present invention. For example, the absorbent material could be in the form of fibers, absorbent swabs, absorbent sheets, or sponge, attached to the embolization coil 16. Absorbent swabs could be formed of firmly integrated fibers.

In some forms, the absorbent material, or the absorbent material strips 32, includes at least one of the following: cotton, such as natural cotton, and regenerated cellulose for occlusion of the body cavity. In certain embodiments, both cotton and regenerated cellulose are included in the absorbent material or the absorbent strips 32. For example, in a preferred embodiment, highly absorbent strips or swabs made by Kettenbach GmbH & Co. KG under the registered trademark Sugi® and including natural cotton and regenerated cellulose are used. The absorbent material may be expandable to grow in physical size upon absorption of bodily fluids. The absorbent material may absorb bodily fluids weighing many times the weight of the absorbent material and growing to many times the original size of the absorbent material. In some embodiments, the absorbent material is configured to absorb bodily fluids that weigh at least, or about, twenty times the weight of the absorbent material. In other embodiments, the absorbent material is configured to absorb bodily fluids that weigh at least seventeen times the weight of the absorbent material, for example, between seventeen and twenty times the weight of the absorbent material.

With reference to FIGS. 1a-1b, the absorbent material is in the form of substantially flat absorbent strips 32. In other words, the absorbent strips 32 have opposed sides or faces lying in planes that are substantially parallel to each other. The strips 32 of absorbent material are spaced apart along the length of the primary coil 18 by a distance L. It should be understood that the distances between each strip 32 need not be equal, and that in some embodiments, the distances between each strip 32 can vary. In other embodiments, it may be desirable to place the strips 32 spaced apart by equal distances L along the length of the primary coil 18.

In some embodiments, the distance L between the strips 32 is at least twice as long as the width w of the strips. In other embodiments, the distance L is at least five times the width w of the strips 32. In preferred embodiments, the length I of each strip 32 is much longer than the width w of each strip 32. The length I can be any desired length, and preferably, the length I is long enough that the strips 32 extend into the lumen 30 of the device 10.

In this embodiment, the length I of the strips 32 in an original size is illustrated as being less than half of the radius of the loops 24. Therefore, the strips 32 only extend partially into the lumen 30 (see FIG. 1b). In some embodiments (e.g., see FIGS. 3a-3d), the length I may extend from the coil 216 to a distance about equal to the radius of the inner lumen 230. In this embodiment, each strip 232 is illustrated as being pinched together at the center 234 of the strip 232 that is located at about half the length I of the strip 232. It may be desirable, in some applications, to use the embodiments with shorter strips 32 of (FIG. 1b) for smaller body vessels and the embodiment with longer strips 232 (FIGS. 3a-3d) for larger body vessels.

With reference to FIG. 1c, the primary coil 18 is shown in a straight configuration, unwound from the shape of the secondary coil 20. The straight configuration may also be the collapsed state of the coil 16 in some embodiments. The strips 32 of absorbent material are substantially flat, but they are pinched together at a center portion 34 to flatten them further at the center portions 34. The strips 32 are pinched by the tightly wound helical turns 22 of the primary coil 18. The strips 32 are held between the helical turns 22 of the primary coil 18 by the initial tension of the primary coil 18 to retain the strips 32 to the primary coil 18. Thus, the strips 32 are attached between, or wedged between, the loops of the primary coil 18 and extend therefrom. In this embodiment, medical grade biocompatible glue 36 also adheres to each strip 32 and attaches each strip 32 to the primary coil 18 of the embolization coil 16. It should be understood that in some embodiments, the tension of the primary coil 18 may be used to retain the strips 32 to the primary coil 18 without the glue 36. In other embodiments, the glue 36 may be used to adhere to and retain the strips 32 to the primary coil 18 without using the tension of the primary coil 18 to pinch the strips 32 between the helical turns 22 of the primary coil 18.

The absorbent, expandable material, which in this embodiment is in the form of strips 32, expands or "grows" to a size much larger than its original size when it soaks up bodily fluids flowing through the vessel 12. For example, in FIG. 1, bodily fluids flow in a direction X through the vessel 12, and the occluding device is configured to absorb the fluids. It should be understood that the absorbent material can have any suitable shape, and in some embodiments, other occluding materials may be added to the embolization coil 16, in addition to the absorbent material described herein. For example, fibers made of an extracellular matrix (ECM) such as small intestinal submucosa (SIS) or other types of submucosa, or fibers of a synthetic, such as Dacron™ (polyester textile fiber) could also be retained by the embolization coil 16.

The strips 32 of absorbent, expandable material are illustrated as being held between every fifth helical turn 22 of the primary coil 18; however, it should be understood that the strips 32 could be attached with any desired length separating them. For example, the strips 32 could be separated by 2, 3, 4, 5, or any number of helical turns 22 or fractions of turns 22.

As shown, the strips 32 take on a generally helical shape consistent with generally helical shape of the secondary coil 20. However, as shown, the strips 32 extend into the lumen 30 of the secondary coil 20. In some embodiments, the strips 32 may be long enough to substantially fill the lumen 30 across the cross-sectional area of the lumen 30.

In one embodiment, the occluding device 10 may comprise at least one or more metals or metal alloys to create variable rigidity along the length of the embolization coil 16. In one embodiment, the embolization coil 16 may comprise platinum and platinum alloys. In another embodiment, the coil 16 may be comprised generally of palladium and the proximal portion may comprise a less rigid alloy, e.g., palladium alloy. In some embodiments, various different metals or alloys may be used, such that portions of the coil 16 have varying stiffnesses. For example, the proximal portion 26 could comprise platinum and be more rigid than the distal portion 28, which could comprise palladium alloy, by way of example. Either portion could also or alternative comprise stainless steel or any other suitable material. In addition, there could be additional portions, beside the proximal and distal portions 26, 28, which could have different stiffnesses, without falling beyond the spirit and scope of the present invention.

For example, at least part of the device 10 may be made of any suitable material including, in one embodiment, a superelastic material, stainless steel wire, cobalt-chromium-nickel-molybdenum-iron alloy, or cobalt-chrome alloy. It is understood that the device 10 may also be formed of any suitable material that will result in a self-opening or self-expanding device 10, such as shape memory materials. Shape memory materials or alloys have the desirable property of becoming rigid, i.e., returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that the material returns to its remembered state. The transition temperature is dependent on the relative proportions of the alloying elements Ni and Ti and the optional inclusion of alloying additives.

In one example, the device 10 may be made of Nitinol with a transition temperature that is slightly below normal body temperature of humans, which is about 98.6° F. Thus, when the device 10 is deployed in a body vessel and exposed to normal body temperature, the alloy of the device 10 will transform to austenite, that is, the remembered state, which for one embodiment of the present invention is the expanded state when the device 10 is deployed in the body vessel. To remove the device 10 it is cooled to transform the material to martensite which is more ductile than austenite, making the device 10 more malleable. As such, the device 10 can be more easily collapsed and pulled into a lumen of a catheter for removal.

In another example, the device 10 may be made of Nitinol with a transition temperature that is above normal body temperature of humans, which is about 98.6° F. Thus, when the device 10 is deployed in a body vessel and exposed to normal body temperature, the device 10 is in the martensitic state so that the device 10 is sufficiently ductile to bend or form into a desired shape. To remove the device 10, the device 10 is heated to transform the alloy to austenite so that it becomes rigid and returns to a remembered state.

Referring now to FIGS. 2a-2b, another occluding device 110 is illustrated. Many features of the occluding device 110 are similar to the occluding device 10 described above, and similar elements have reference numerals that are the same number, except with a "one" in front of them. For example, occluding device 10 is now numbered occluding device 110. Accordingly, it should be understood that any of the options and examples described above with respect to occluding device 10 could also or alternatively be used with occluding device 110. Likewise, features described in connection with occluding device 110 could be used in addition to, or in the alternative to, features described with respect to occluding device 10.

The occluding device 110 of FIGS. 2a-2b has an embolization coil 116 that has a generally helical shape. The embolization coil 116 includes a primary coil 118 having a plurality of helical turns 122. The primary coil 118 is wound into a secondary coil 120 having a series of helical loops 124. In this embodiment, the loops 124 of the embolization coil 116 do not contact each other in the expanded state of the occluding device 110. Thus, the embolization coil 116 has a series of axially spaced apart loops 124. The loops 124 may be spaced apart by a predetermined distance, for example, by about four to five millimeters curl space, in some embodiments, wherein the curl space is defined as the distance between two loops 124. It should be understood, however, that the helical turns or loops 124 of the embolization coil 116 could contact each other in the expanded state, without falling beyond the spirit and scope of the present invention.

Although a primary coil 118 and a secondary coil 124 are illustrated, other configurations of the embolization coil 116 may also be used, without falling beyond the spirit and scope of the present invention. For example, in some embodiments, there could be no primary coil, and instead, the embolization coil could consist of a large helical coil formed from a solid wire, cannula, or bar, by way of example. The series of loops 124 define a cross-sectional inner lumen 130 through the secondary coil 120 of the embolization coil 116.

The occluding device 110 includes absorbent, expandable material attached to the embolization coil 116. In this embodiment, the absorbent material is in the form of a plurality of strips 132 of absorbent material attached to the embolization coil 16 and extending therefrom. With reference to FIGS. 2a-2b, only some of the strips 132 are labeled, to avoid cluttering the figures with a large duplication of reference numbers. The absorbent material strips 132 may be formed of cotton and regenerative cellulose, or have any other make-up and/or configuration as described above with respect to the absorbent material and absorbent strips 32.

The absorbent material is illustrated in the form of substantially flat absorbent strips 132. In other words, the absorbent strips 132 have opposed sides or faces lying in planes that are substantially parallel to each other. The strips 132 of absorbent material are spaced apart along the length of the embolization coil 116 by a distance $L_2$. It should be understood that the distances between each strip 132 need not be equal, and that in some embodiments, the distances between each strip 132 can vary. In other embodiments, it may be desirable to place the strips 132 spaced apart by equal distances $L_2$ along the length of the coil 116.

The absorbent, expandable material, which in this embodiment is in the form of strips 132 expands or "grows" to a size much larger than its original size when it soaks up bodily fluids flowing through the vessel 112. For example, with reference to FIGS. 2a-2b, bodily fluids flow in a direction X through the vessel 112, and the occluding device 110 is configured to absorb the fluids. FIG. 2b illustrates that the strips 132 having expanded from soaking up fluid in the body vessel 112, such that the strips 132 now have an expanded size. It should be understood that the strips 132 could expand much larger as they soak up additional fluid, and they may hold up to and including 20 times their own weight in bodily fluids, or greater. As the strips 132 absorb fluid and "grow", they occlude more of the lumen 130 than they did in their original sizes, therefore resulting in an improved occlusion of the body vessel 112.

Each strip 132 has portions defining an aperture 138 through the strip 132. The coil 116 is threaded through and extends through the aperture 138 to hold and retain the strip 132 on the coil 116. The apertures 138 may be preformed or pre-made in the strips 132, or the strips 132 may be punctured by the coil 116 to create the apertures 138. In some embodiments, the strips 132 are retained to the coil 116 by virtue of the coil being threaded through the apertures 138, and therefore, no glue 36 is needed, and/or it is not necessary to retain the strips 132 to the coil by tension between helical turns of the coil. However, in other embodiments, a combination of retaining items and methods may be used. For example, the strips 132 may be held to the coil 116 through their apertures 138, and they may also use glue or coil turns 122 to hold the strips 132 to the coil 116 (shown in FIG. 1c) with respect to the primary coil 18 of the embolization coil 16.

Now with reference to FIGS. 3a-3d, another occluding device 210 is illustrated. Many features of the occluding device 210 are similar to the occluding devices 10, 110 described above, and similar elements have reference numerals that end in the same two numbers, but have a "two" in front of them. For example, occluding device 10, 110 is now numbered occluding device 210. Accordingly, it should be understood that any of the options and examples described above with respect to occluding devices 10, 110 could also or alternatively be used with occluding device 210. Likewise, features described in connection with occluding device 210 could be used in addition to, or in the alternative to, features described with respect to the occluding devices 10, 110.

The occluding device 210 of FIGS. 3a-3d has an embolization coil 216 that has a generally helical shape similar to the embolization coils 16, 116 described above. For example, the embolization coil 216 includes a primary coil 218 having a plurality of helical turns 222, the primary coil 218 being wound into a secondary coil 220 having a series of helical loops 224. The series of loops 224 define a cross-sectional inner lumen 230 through the secondary coil 220 of the embolization coil 216 in the expanded state of the occlusion device 210. In this embodiment, the inner lumen 230 has a generally circular cross-sectional shape.

The occluding device 210 includes absorbent, expandable material attached to the embolization coil 216. In this embodiment, the absorbent material is in the form of a plurality of sheets 232 of absorbent material attached to the embolization coil 16 and extending therefrom. With reference to FIGS. 3a-3d, only some of the sheets 232 are labeled, to avoid cluttering the figures with a large duplication of reference numbers. The absorbent material sheets 232 may be formed of cotton and regenerative cellulose, or have any other make-up and/or configuration as described above with respect to the absorbent material and absorbent strips 32.

The absorbent material is illustrated in the form of substantially flat absorbent sheets 232. In other words, the absorbent sheets 232 have opposed sides or faces lying in planes that are substantially parallel to each other. The sheets 232 of absorbent material may be spaced apart along the length of the embolization coil 216 by a distance L or $L_2$ (L is shown in FIG. 1a, and $L_2$ is shown in FIG. 2a).

In this embodiment, each sheet 232 has a length $l_2$. Each sheet 232 is connected to the coil 216 at a point near an edge 260 of each sheet 232, and the majority of the length $l_2$ of each sheet 232 extends into the inner lumen 230 of the secondary coil 220. Each sheet 232 extends into the lumen 230 to a distance that is greater than or equal to the radius r of the lumen 230. Thus, $l_2$ is greater than the radius r, because some of the length $l_2$ of each sheet 232 is pinched together in the helical turns 222 of the primary coil 218, and a substantially negligible portion of each sheet 232 extends to the outside of the coil lumen 230 at the edge 260 of each sheet 232. Thus, the sheets 232 overlap or touch at the central axis C of the lumen 230.

The absorbent, expandable material, which in this embodiment is in the form of strips 132 expands or "grows" to a size much larger than its original size when it soaks up bodily fluids flowing through the vessel 212. For example, with reference to FIGS. 3a and 3c, bodily fluids flow in a direction X through the vessel 212, and the occluding device 210 is configured to absorb the fluids. FIGS. 3c-3d illustrate the sheets 232 having expanded from soaking up fluid in the body vessel 212. It should be understood that the sheets 232 could expand much larger as they soak up additional fluid, and they may hold up to and including 20 times their own weight in bodily fluids. As the sheets 232 absorb fluid and "grow", they occlude more of the lumen 230 than they did in their original size, and therefore result in an improved occlusion of the body vessel 212. Thus, each sheet 232 has an original size, as shown in FIGS. 3a-3b, and an expanded size, as shown in FIGS. 3c-3d.

In this embodiment, the sheets 232 form a barrier completely extending across the lumen 230 when the sheets 232 have expanded after soaking up fluid, in the expanded size. The sheets 232 block the lumen 230 across its entire cross-section. Since the coil 216 contacts the vessel wall 214 at all edges of the vessel wall 214 (see FIG. 3d), the body vessel 212 is completely blocked. Since the strips 32, 132 of FIGS. 1a-2b also "grow" or expand upon soaking up fluid, those strips 32, 132 could also form a barrier that completely extends across the lumen 30, 130 when the strips 32, 132 have expanded.

FIGS. 4a-4c illustrate a body cavity embolization kit 240 which implements the occluding device 10, 110, 210 in accordance with one embodiment of the present invention. As shown, the kit 240 includes an inner catheter 242 preferably made from a soft, flexible material such as silicone or any other suitable material. Generally, the inner catheter 242 has a proximal end 244, a distal end 246, and a plastic adapter or hub to receive an apparatus to be advanced therethrough. In this embodiment, the inside diameter of the inner catheter 242 may range between 0.014 and 0.027 inch. The kit 240 further includes a guide wire 248 which provides the guide catheter 250 a path during insertion of the guide catheter 250 within a body cavity. The size of the guide wire 248 is based on the inside diameter of the guide catheter 250.

In this embodiment, the kit 240 further includes a polytetrafluoroethylene (PTFE) guide catheter or sheath 250 for percutaneously introducing the inner catheter 242 in a body cavity. Of course, any other suitable material may be used without falling beyond the scope or spirit of the present invention. The guide catheter 250 may have a size of about 4-French to 8-French and allows the inner catheter 242 to be inserted therethrough to a desired location in the body cavity. The guide catheter 250 receives the inner catheter 242 and provides stability of the inner catheter 242 at a desired location of the body cavity. For example, the guide catheter 250 may stay stationary within a common visceral artery, e.g., a common hepatic artery, and add stability to the inner catheter 242 as the inner catheter 242 is advanced through the guide catheter 250 to a point of occlusion in a connecting artery, e.g., the left or right hepatic artery.

When the distal end 246 of the inner catheter 242 is at the point of occlusion in the body cavity, the occluding device (e.g., 10, 110, 210) is loaded at the proximal end 244 of the inner catheter 242 and is advanced through the inner catheter 242 for deployment through the distal end 246. The occluding device 10, 110, 210 may be advanced over the guide wire 248, or the guide wire 248 may be removed and replaced by the occluding device 10, 110, 210. In this embodiment, a push wire 252 is used to mechanically advance or push the occluding device 10, 110, 210 through the inner catheter 242. The size of the push wire 252 used depends on the diameter of the inner catheter 242.

The occluding device 10, 110, 210 is collapsed into the collapsed state in the inner catheter 242, such that the primary coil 18, 118, 218 is still wound and has helical turns, but the embolization coil 16, 116, 216 is collapsed into an approximately linear configuration, such that the secondary coil 20, 120, 220 is not present until the embolization coil 16, 116, 216 is deployed from the catheter 242. In other words, the embolization coil 16 may lay in a substantially linear configuration in the collapsed state, as shown in FIG. 1c. The occluding device 10, 110, 210 is shown extending in a linear configuration from the catheter 242 in FIG. 4c to illustrate the configuration in which the device 10, 110, 210 exists in the catheter 242, but it should be understood that once the device 10, 110, 210 is deployed from the inner catheter 242, the embolization coil 16, 116, 216 would begin to curl into the shape of the secondary coil 20, 120, 220 having loops 24, 124, 224.

It is to be understood that the body cavity embolization kit 240 described above is merely one example of a kit that may be used to deploy the occluding device in a body vessel. Of course, other kits, assemblies, and systems may be used to deploy any embodiment of the occluding device 10, 110, 210 without falling beyond the scope or spirit of the present invention.

The occluding device 10, 110, 210 may be deployed in a body vessel 12, 112, 212 by a push embolization method or a squirt embolization method in accordance with the present invention. The kit 240 may or may not be used. As typically performed in embolotherapy, an introducer or the guide catheter 250 is percutaneously introduced into the body vessel 12, 112, 212 of a patient and the inner catheter 242 is passed through the guide catheter 250 to position the inner catheter 242 at a desired point of occlusion in the body vessel 12, 112, 212.

The occluding device 10, 110, 210 may be deployed within the body vessel 12, 112, 212 in any suitable manner. In one example, the occluding device 10, 110, 210 which is elongated to its full length within a cartridge, is loaded in the hub at the proximal end 244 of the inner catheter 242. The device 10, 110, 210 is advanced by the pusher wire 252 in accordance with this method of deploying the occluding device 10, 110, 210. The distal portion 28 of the occluding device 10, 110, 210, e.g., a first loop 24, 124, 224 of the secondary coil 20, 120, 220 is deployed at the desired point of occlusion in the body vessel 12, 112, 212 as a remaining portion of the occluding device 10, 110, 210 is held in the inner catheter 242. The first portion of the coil 16, 116, 216 may be between about 5% to 10% of the length of the coil 16, 116, 216. The first portion begins to hold the device 10, 110, 210 in place within the vessel 12, 112, 212. The location of the distal portion 28 in the body vessel 12, 112, 212 is ascertained by any suitable means, such as by fluoroscopy, relative to the body vessel 12, 112, 212. When the distal portion 28 is at the desired point of occlusion in the body vessel 12, 112, 212, the proximal portion 26 is folded across the lumen of the body vessel 12, 112, 212 to pack the coil 16, 116, 216 and occlude the body vessel 12, 112, 212. In some embodiments, the proximal portion 26 may be folded within the distal portion 28, if desired, by moving the catheter 250 reciprocally back and forth relative to the body vessel 12, 112, 212 as the proximal portion 26 is deployed from the inner catheter 242.

As a length of the proximal portion 26 is being deployed, the distal end 246 of the inner catheter 242 is moved back. The inner catheter 242 is then moved forward against the length of the proximal portion 26, thereby folding the length of the proximal portion 26 at the desired point of occlusion. The inner catheter 242 is moved back and forth until the proximal portion 26 is folded within the distal portion 28 and the occluding device 10, 110, 210 is in a packed state.

However, if it is ascertained that the distal portion 28 of the occluding device 10, 110, 210 is not at the desired point of occlusion, then the position of the inner catheter 242 is moved fore or aft relative to the body vessel 12, 112, 212 such that the distal portion 28 is placed at the desired point of occlusion.

In a squirt embolization method of transcatheter embolization using an embodiment of the occluding device 10, 110, 210 of the present invention, a guide catheter 250 is introduced into the body vessel 12, 112, 212 as described above in the push embolization method. Once the inner catheter 242 is passed through the guide catheter 250 and the occluding device 10, 110, 210 is loaded at the hub of the inner catheter 242, the occluding device 10, 110, 210 is advanced through the inner catheter 242 with use of a luer lock syringe and saline solution, for example. A first portion of the distal portion 28, e.g., a first loop 24, 124, 224 of the secondary coil 20, 120, 220 is deployed at the desired point of occlusion in the body vessel 12, 112, 212 as a remaining portion of the distal portion 28 is held in the inner catheter 242. The first portion of the coil 16, 116, 216 may be between about 5% to 10% of the length of the coil 16, 116, 216.

The location of the distal portion 28 in the body vessel 12, 112, 212 is ascertained by any suitable means, such as by fluoroscopy, relative to the body vessel 12, 112, 212. If the deployed portion of the coil 16, 116, 216 is at the desired point of occlusion in the body vessel 12, 112, 212, then the remaining portion is introduced together with the saline solution. The distal portion 28 may hold the device 10, 110, 210 in place within the vessel 12, 112, 212. Then, the proximal portion 26 may be packed within the distal portion 28, if desired, to occlude the body vessel 12, 112, 212. In other embodiments, no packing may be done, and the coil 16, 116, 216 may remain as shown in FIGS. 1a, 2a, 2b, 3a, and 3c.

While the present invention has been described in terms of preferred embodiments, it will be understood, of course, that the invention is not limited thereto since modifications may be made to those skilled in the art, particularly in light of the foregoing teachings. Such variations are not to be regarded as a departure from the spirit and scope of the present disclosure.

We claim:

1. An occluding device for occlusion of a body cavity, the device comprising:
   an embolization coil formed from at least one wire strand, the embolization coil having a proximal portion and a distal portion extending longitudinally from the proximal portion, the embolization coil having an initial tension along the distal and proximal portions, the embolization coil being defined by a primary coil formed into a secondary coil, the primary coil having a primary shape defined by a linear longitudinally extending coil having a plurality of helical turns, the primary coil being helically wound into the secondary coil, the secondary coil having a series of axially spaced apart loops, the axially spaced apart loops being larger than the helical turns of the primary coil, and forming an inner lumen therethrough, the inner lumen being generally circular in cross-sectional shape, defining a central axis and a radius, the embolization coil being movable between an expanded state for occlusion of a body cavity and a collapsed state for delivery or retrieval; and
   absorbent material attached to the embolization coil and extending therefrom, the absorbent material being in the form of substantially flat strips, each of the flat strips having a pair of flat opposed ends and a length therebetween, the strips being attached at one of the opposed ends between two adjacent loops of the primary coil, wherein the length of each strip extends from the primary coil into the inner lumen of the secondary coil in a direction transverse to the central axis of the inner lumen at a distance that is greater than or equal to the radius of the inner lumen so that the other opposed ends of the strips overlap or touch at the central axis, the flat strips including at least one of cotton and regenerated cellulose for occlusion of the body cavity.

2. The occluding device of claim 1, the absorbent material being expandable to grow in physical size upon absorption of bodily fluids.

3. The occluding device of claim 1, wherein the absorbent material is configured to absorb bodily fluids, the absorbent material being configured to absorb bodily fluids that weigh at least twenty times the weight of the absorbent material.

4. The occluding device of claim 1, the absorbent material comprising both regenerated cellulose and cotton.

5. The occluding device of claim 1, wherein the strips of absorbent material are spaced apart along the length of the primary coil.

6. The occluding device of claim 5, wherein the helical turns of the primary coil are tightly wound and contact each other, the absorbent strips being held between the helical turns of the primary coil by the initial tension of the primary coil.

7. The occluding device of claim 1, wherein each strip is adhered to the embolization coil with biocompatible glue.

8. The occluding device of claim 5, wherein adjacent strips are spaced apart by a distance corresponding to at least about twice the length of each strip.

9. An occluding device for occlusion of a body cavity, the device comprising:
an embolization coil formed from at least one wire strand, the embolization coil having a proximal portion and a distal portion extending longitudinally from the proximal portion, the embolization coil having an initial tension along the distal and proximal portions, the embolization coil being defined by a primary coil formed into a secondary coil, the primary coil having a primary shape defined by a linear longitudinally extending coil having a plurality of helical turns, the primary coil being helically wound into the secondary coil, the secondary coil having a series of axially spaced apart loops, the axially spaced apart loops being larger than the helical turns of the primary coil and forming an inner lumen therethrough, the inner lumen being generally circular in cross-sectional shape, defining a central axis and a radius, the embolization coil being movable between an expanded state for occlusion of a body cavity and a collapsed state for delivery or retrieval; and
a plurality of substantially flat strips of absorbent material attached to the embolization coil and extending therefrom, each strip having a pair of flat opposed ends, the strips being attached at one of the opposed ends between two adjacent loops of the primary coil wherein the length of each strip extends from the primary coil into the inner lumen of the secondary coil in a direction transverse to the central axis of the inner lumen at a distance that is greater than or equal to the radius of the inner lumen so that the other opposed ends of the strips overlap or touch at the central axis, the flat strips being individually spaced apart longitudinally along the embolization primary coil for occlusion of the body cavity.

10. The occluding device of claim 9, wherein the strips of absorbent material are configured to absorb bodily fluids, each strip being configured to absorb bodily fluids that weigh at least twenty times the weight of the strip.

11. The occluding device of claim 9, the strips of absorbent material comprising both regenerated cellulose and cotton.

12. The occluding device of claim 11, wherein the helical turns of the primary coil are tightly wound and contact each other, the strips being held between the helical turns of the primary coil by the initial tension of the primary coil.

13. An embolization kit for occluding fluid flow through a body vessel, the kit comprising:
a guide catheter;
an inner catheter having proximal and distal ends and being configured to be passed through the guide catheter to position the inner catheter in the body vessel, the inner catheter having a hub adjacent the proximal end; and
an occluding device disposed coaxially within the inner catheter, the occluding device comprising:
an embolization coil formed from at least one wire strand, the coil having a proximal portion and a distal portion extending longitudinally from the proximal portion, the embolization coil having an initial tension along the distal and proximal portions, the embolization coil being defined by a primary coil formed into a secondary coil, the primary coil having a primary shape defined by a linear longitudinally extending coil having a plurality of helical turns, the primary coil being helically wound into the secondary coil, the secondary coil having a series of axially spaced apart loops, the axially spaced apart loops being larger than the helical turns of the primary coil and forming an inner lumen therethrough, the inner lumen being generally circular in cross-sectional shape, defining a central axis and a radius, the embolization coil being movable between an expanded state for occlusion of a body cavity and a collapsed state for delivery or retrieval; and
a plurality of substantially flat strips of expandable material attached to the coil and extending therefrom, each of the flat strips having a pair of flat opposed ends, the strips of expandable material being spaced apart longitudinally along the coil for occlusion of the body cavity and being attached at one of the flat opposed ends between two adjacent loops of the primary coil, wherein the length of each strip extends from the primary coil into the inner lumen of the secondary coil in a direction transverse to the central axis of the inner lumen at a distance that is greater than or equal to the radius of the inner lumen so that the other opposed ends of the strips overlap or touch at the central axis, each strip of expandable material comprising regenerated cellulose and cotton.

14. The embolization kit of claim 13 wherein the guide catheter is between about 4-French and 8-French.

15. The embolization kit of claim 13, further comprising a pusher wire for advancing the occluding device.

* * * * *